(12) United States Patent
Corson

(10) Patent No.: US 7,761,241 B2
(45) Date of Patent: *Jul. 20, 2010

(54) RAPID SCANNING TECHNIQUE

(75) Inventor: John F. Corson, Mountain View, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 1010 days.

This patent is subject to a terminal disclaimer.

(21) Appl. No.: 11/503,756

(22) Filed: Aug. 14, 2006

(65) Prior Publication Data

US 2007/0171411 A1  Jul. 26, 2007

Related U.S. Application Data

(60) Provisional application No. 60/760,434, filed on Jan. 20, 2006.

(51) Int. Cl.
*G06F 19/00* (2006.01)
*G06F 15/00* (2006.01)

(52) U.S. Cl. ............................................. 702/19; 700/1

(58) Field of Classification Search ....................... None
See application file for complete search history.

(56) References Cited

U.S. PATENT DOCUMENTS

| 6,078,390 | A | 6/2000 | Bengtsson |
| 6,927,389 | B2 | 8/2005 | Curry et al. |
| 6,952,008 | B2 | 10/2005 | Corson |
| 2004/0021911 | A1 | 2/2004 | Corson et al. |
| 2004/0061049 | A1* | 4/2004 | Curry et al. ............. 250/282 |

* cited by examiner

*Primary Examiner*—John S Brusca

(57) ABSTRACT

Disclosed herein is a computer programmed to carry out a method for reducing directional error in scanned intensity values. The method includes scanning some rows of a substrate in a first direction, and some rows of the substrate in a second, different, direction, in order to obtain intensity values exhibited by various regions of the various rows. The intensity values from rows scanned in the first direction are analyzed, and the intensity values from rows scanned in the second direction are analyzed, in order to determine the directional error. The intensity values from rows scanned in the first direction and the intensity values from rows scanned in the second direction are then adjusted to reduce the directional error.

20 Claims, 7 Drawing Sheets

RAPID SCANNING TECHNIQUE

RELATED APPLICATIONS

This application claims priority from Provisional Application Ser. No. 60/760,434, entitled "RAPID SCANNING TECHNIQUE," filed Jan. 20, 2006, and which is incorporated herein by reference.

BACKGROUND

Fluorescence readers are often used for re-sequencing or gene expression studies. In these systems, light such as that from a laser is directed onto a target, which may include molecules capable of fluorescing. Of course, the light could come from the process of chemi-luminescence as well. The emitted fluorescent light is then detected and analyzed. Oftentimes, multiple color dyes are utilized. For example, four colors may be used. The light is detected by florescence detection devices such as confocal scanning microscopes and imagers that utilize detection elements such as photomultiplier tubes (PMTs), avalanche photo-diodes (APDs), and charge-coupled devices (CCDs).

The data obtained from fluorescent readers are subject to certain forms of error. For example, unintended sources of electromagnetic radiation (e.g., sources of radiation other than the fluorescent molecules on the target) may emit light that is received by the reader, and interpreted as having originated from the target. Additionally, the reader may include automatic gain control circuitry that improperly amplifies or attenuates the received signal, based upon the intensity of emitted light from regions of the target having been read during a previous period of time. Either source of error causes the reader to associate a given region of the target with an erroneously high or low radiation intensity value. Other sources of errors exist, and these sources of errors also reduce the reliability of the information developed by the reader. Such other sources of error include, without limitation, autofocus error that places the focal plane differently for right-going and left-going scans, and mechanical torque of the optical components during motion, which tends to change the optical gain depending on the scan direction.

Typically, a fluorescent reader scans a surface of the target on a line-by-line basis, proceeding either left-to-right or right-to-left while scanning a given line. (Of course, the reader may scan the surface on a line-by-line basis, proceeding up-to-down, or down-to-up, or in any generally linear direction. Usually, the linear direction is chosen so as to permit relatively fast scanning). It has been observed that some sources of error exhibit a correlation to the direction in which the scanning occurs. Accordingly, some scanning techniques have been developed to reduce errors related to direction of scan (some of these techniques also reduce the Gaussian noise exhibited in the received signal). Unfortunately, these techniques may be slow under certain circumstances.

As suggested by the foregoing, there exists an opportunity for an improved scanning technique. Such an improved scanning technique may reduce sources of error related to direction of scan, may be performed relatively quickly, and may be relatively inexpensive.

SUMMARY

In general terms, the present invention is directed to a scanning technique for a fluorescence reader. The technique reduces the level of direction-dependent error observed in a data set yielded from the reader.

According to some embodiments, a computerized method of scanning a plurality of fluorescent regions of a substrate includes scanning a first plurality of rows in a first direction, thereby obtaining a first plurality of fluorescent intensity values. Each value in the first plurality of fluorescent intensity values corresponds to regions in the first plurality of rows. A second plurality of rows is scanned in a second direction that is opposite the first direction, thereby obtaining a second plurality of fluorescent intensity values. Each value in the second plurality of fluorescent intensity values corresponds to regions in the second plurality of rows. Quantities standing in known relation to the first and second plurality of fluorescent intensity values are adjusted to reduce directional errors observed in the first and second plurality of fluorescent intensity values.

According to other embodiments, a computer may include a processor and a memory in communication therewith. The memory stores a set of instructions that when executed cause the processor to scan a first plurality of rows in a first direction, thereby obtaining a first plurality of fluorescent intensity values. Each value in the first plurality of fluorescent intensity values corresponds to regions in the first plurality of rows. Also, a second plurality of rows is scanned in a second direction that is different from the first direction, thereby obtaining a second plurality of fluorescent intensity values. Each value in the second plurality of fluorescent intensity values corresponds to regions in the second plurality of rows. Quantities standing in known relation to the first and second plurality of fluorescent intensity values are adjusted to reduce directional errors observed in the first and second plurality of fluorescent intensity values.

DETAILED DESCRIPTION

Definitions

Figure 1:
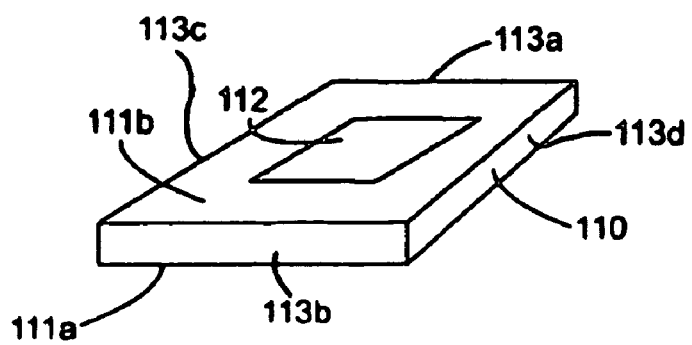
FIG. 1 is a perspective view of an exemplary embodiment of an array package including a substrate carrying a typical array, as may be used in connection with embodiments of scanning techniques described herein.

Unless defined otherwise, all technical and scientific terms used herein have the same meaning as commonly understood by one of ordinary skill in the art to which this invention belongs. Still, certain elements are defined below for the sake of clarity and ease of reference.

The term "biomolecule" means any organic or biochemical molecule, group or species of interest. Exemplary biomolecules include peptides, proteins, amino acids and nucleic acids.

The term "peptide" as used herein refers to any compound produced by amide formation between a carboxyl group of one amino acid and an amino group of another amino acid.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g., deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "nucleoside" and "nucleotide" are intended to include those moieties that contain not only the known purine and pyrimidine base moieties, but also other heterocyclic base moieties that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like, or form bicyclic derivatives, as in locked nucleic acids.

The terms "ribonucleic acid" and "RNA" as used herein refer to a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

A "biopolymer" is a polymeric biomolecule of one or more types of repeating units. Biopolymers are typically found in biological systems and particularly include polysaccharides (such as carbohydrates), peptides (which term is used to include oligopeptides, polypeptides and proteins) and nucleic acids (which term is used to include oligonucleotides and polynucleotides) as well as their analogs such as those compounds composed of or containing amino acid analogs or non-amino acid groups, or nucleotide analogs or non-nucleotide groups.

A "biomonomer" references a single unit, which can be linked with the same or other biomonomers to form a biopolymer (e.g., a single amino acid or nucleotide with two linking groups, one or both of which may have removable protecting groups).

An "array," includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. In the broadest sense, the arrays of many embodiments are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, DNAs, RNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm, and usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 110 may transmit at least 20%, or 50% (or even at least 70%, 90%, or 95%), of the illuminating light incident on the front as may be measured across the entire integrated spectrum of such illuminating light, or alternatively at 532 nm or 633 nm or other selected wavelengths.

Arrays can be fabricated using drop deposition from pulse-jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. These references are incorporated herein by reference. Other drop deposition methods can be used for fabrication, as previously described herein.

The term "sample" as used herein relates to a material or mixture of materials, typically, although not necessarily, in fluid form, containing one or more components of interest.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

Figure 2:
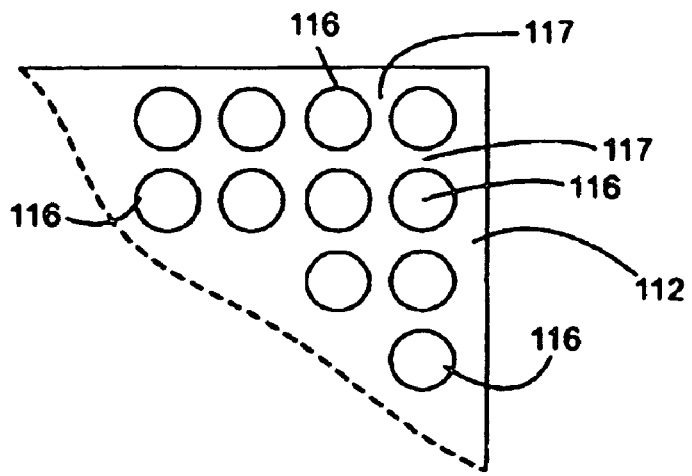
FIG. 2 is an enlarged view of a portion of FIG. 1 showing some of the identifiable individual regions of a single array of FIG. 1.
Figure 3:
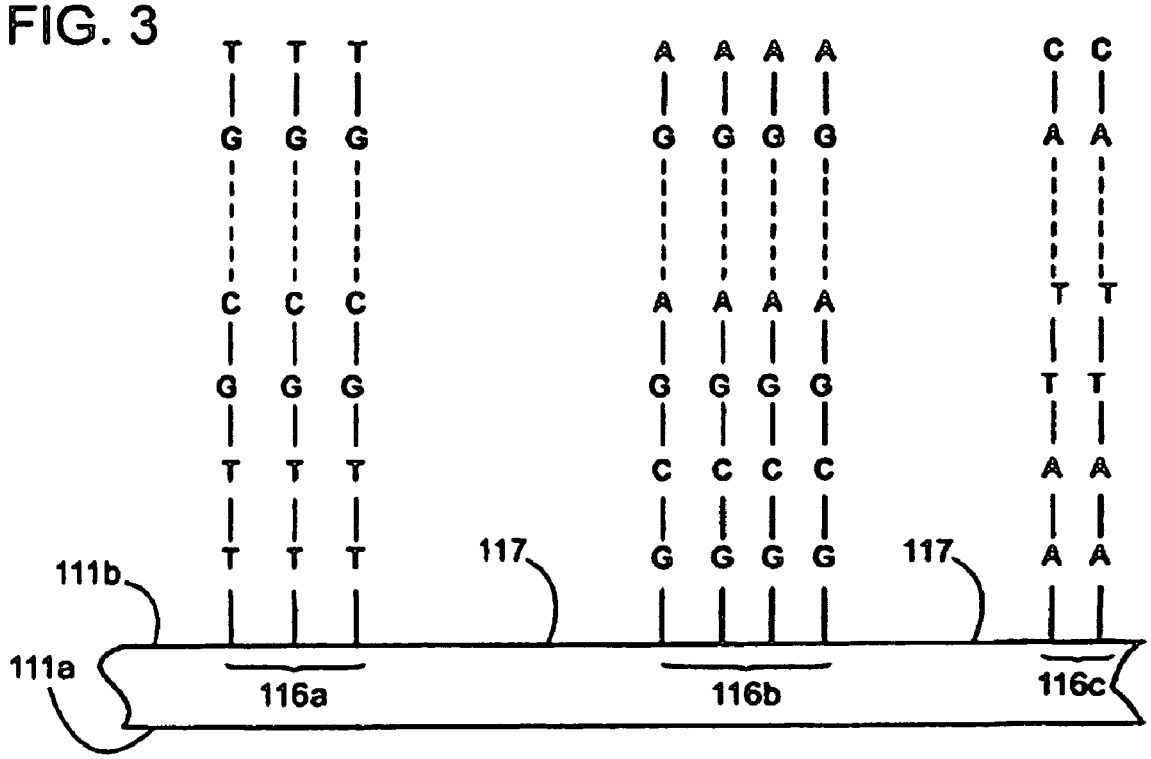
FIG. 3 depicts an enlarged cross-section of a portion of FIG. 2.

An exemplary array is shown in FIGS. 1-3, where the array shown in this representative embodiment includes a contiguous planar substrate 110 carrying an array 112 disposed on front surface 111*b* of substrate 110. It will be appreciated though, that more than one array (any of which are the same or different) may be present on front surface 111*b*, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 usually cover only a portion of the front surface 111*b*, with regions of the front surface 111*b* adjacent the opposed sides 113*c*, 113*d* and leading end 113*a* and trailing end 113*b* of slide 110, not being covered by any array 112. A rear surface 111*a* of the slide 110 does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of biopolymers, e.g., in the form of polynucleotides. As mentioned above, all of the features 116 may be different, or some or all could be the same. The interfeature areas 117 could be of various sizes and configurations, or there may be no interfeature area 117 present, that is features 116 may be directly adjacent to one another. Each feature carries a predetermined biopolymer such as a predetermined oligonucleotide (which includes the possibility of mixtures of oligonucleotides). It will be understood that there may be a linker molecule (not shown) of any known types between the rear surface 111*b* and the first nucleotide.

Substrate 110 may carry on rear or front surface 111*a* or 111*b*, an identification code, e.g., in the form of bar code (not shown) or the like printed on a substrate in the form of a paper label attached by adhesive or any convenient means. The identification code contains information relating to array 112, where such information may include, but is not limited to, an identification of array 112, i.e., layout information relating to the array(s), etc.

Figure 4:
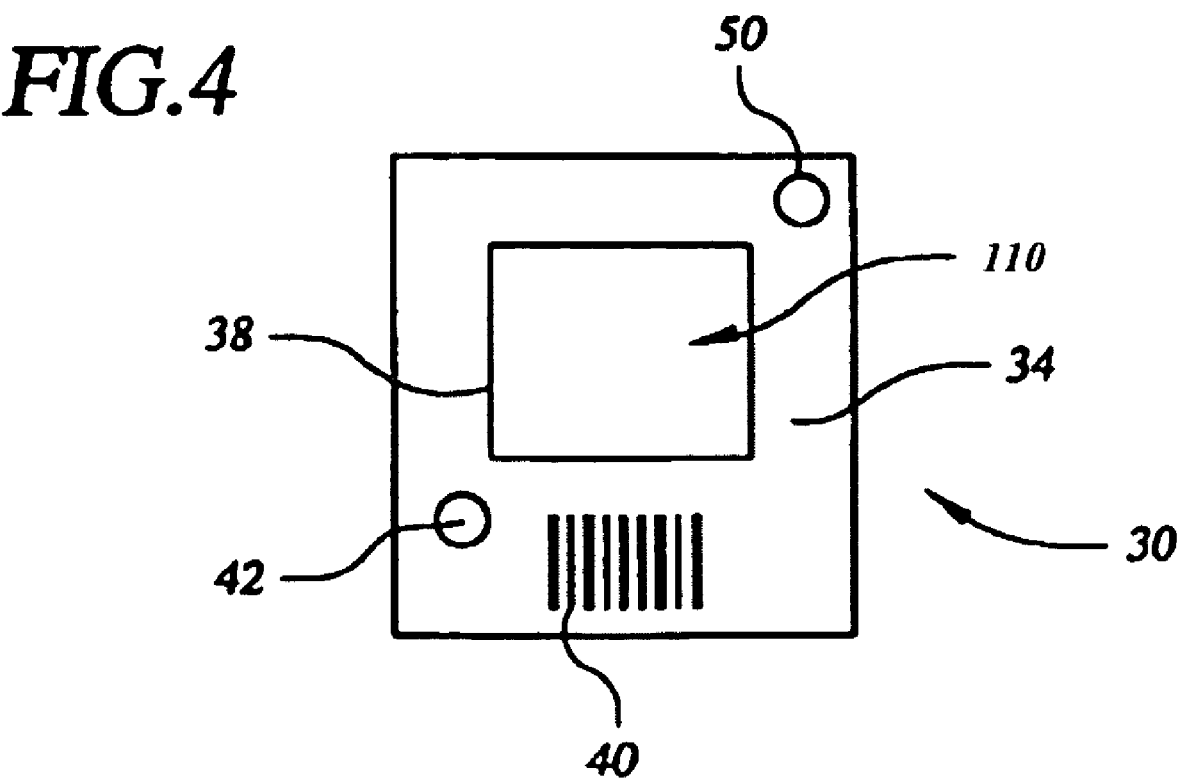
FIG. 4 depicts a front view of another array package in the form of a cartridge, which may be used in the present invention.

Referring now to FIG. 4 an array package 30 may include a housing 34 which has received substrate 110 adjacent an opening. Substrate 110 is sealed (such as by the use of a suitable adhesive) to housing 34 around a margin 38 with the rear surface 111*a* facing outward. Housing 34 is configured such that housing 34 and substrate 110, define a chamber into which features 116 of array 112 face. This chamber is accessible through resilient septa 42, 50 which define normally closed ports of the chamber. In this case array package 30 may be associated with the identifier 40 by providing identifier 40 on housing 34. Throughout this application "association" of any these or other items with the array, can be accomplished, for example, by the items being present in the same package as the array when shipped to an end user.

The components of the embodiments of either array package 30 described above, may be made of any suitable material. For example, housing 34 can be made of metal or plastic such as polypropylene, polyethylene or acrylonitrile-butadiene-styrene ("ABS"). Substrate 110 may be of any suitable material, and is preferably sufficiently transparent to the wavelength of an interrogating and array emitted light, as to allow interrogation without removal from housing 34. Such transparent and non-transparent materials include, for flexible substrates: nylon, both modified and unmodified, nitrocellulose, polypropylene, and the like. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like). The front surface 111*b* of substrate 110 may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), The materials from which substrate 110 and housing 34 (at least the portion facing toward the inside of chamber 36) may be fabricated should ideally themselves exhibit a low level of binding during hybridization or other events.

In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

The term "substrate" as used herein refers to a surface upon which marker molecules or probes, e.g., an array, may be adhered. Glass slides are the most common substrate for use in connection with the subject matter of the present document, although fused silica, silicon, plastic and other materials are also suitable.

DESCRIPTION OF THE EMBODIMENTS

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Figure 5:
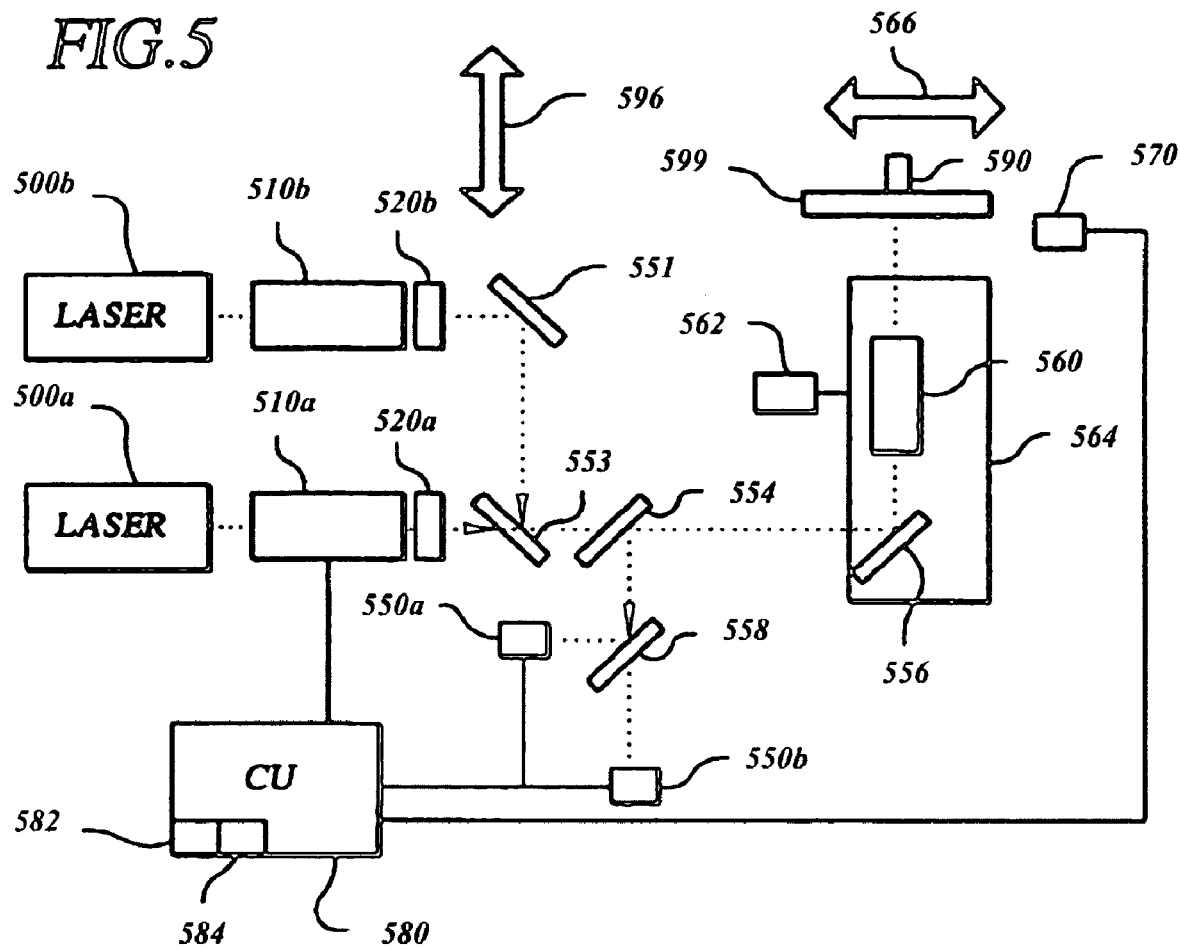
FIG. 5 schematically illustrates an exemplary embodiment of apparatus that may employ various embodiments of the scanning techniques disclosed herein.

Referring now to FIG. 5, an apparatus of the present invention (which may be generally referenced as an array "scanner") is illustrated. A light system provides light from a laser 500 which passes through an electro-optic modulator (EOM) 510 with attached polarizer 520. Each laser 500a, 500b may be of different wavelength (for example, one providing red light and the other green) and each has its own corresponding EOM 510a, 510b and polarizer 520a, 520b. The beams may be combined along a path toward a holder 599 by the use of full mirror 551 and dichroic mirror 553. A control signal in the form of a variable voltage applied to each corresponding EOM 510a, 510b by the controller (CU) 580, changes the polarization of the exiting light which is thus more or less attenuated by the corresponding polarizer 520a, 520b. Controller 580 may be or include a suitably programmed processor. Thus, each EOM 110 and corresponding polarizer 520 together act as a variable optical attenuator which can alter the power of an interrogating light spot exiting from the attenuator in a manner, and for purposes, such as described in U.S. Pat. No. 6,406,849, the disclosure of which is herein incorporated by reference. The remainder of the light from both lasers 500a, 500b is transmitted through a dichroic beam splitter 554, reflected off fully reflecting mirror 556 and focused onto either an array 112 of an array package 30 mounted on holder 599, or a calibration member, whichever is at a reading position, using optical components in beam focuser 560. Light emitted, in particular fluorescence, at two different wavelengths (for example, green and red light) from features 116, in response to the interrogating light, is imaged using the same optics in focuser/scanner 560, and is reflected off mirrors 556 and 554. The two different wavelengths are separated by a further dichroic mirror 558 and are passed to respective detectors 550a and 550b. More optical components (not shown) may be used between the dichroic and each detector 550a, 550b (such as lenses, pinholes, filters, fibers etc.) and each detector 550a, 550b may be of various different types (e.g. a photomultiplier tube (PMT) or a CCD or an avalanche photodiode (APD)). All of the optical components through which light emitted from an array 112 or calibration member in response to the illuminating laser light, passes to detectors 550a, 550b, together with those detectors, form a detection system. This detection system has a fixed focal plane.

A scan system causes the illuminating region in the form of a light spot from each laser 500a, 500b, and a detecting region of each detector 550a, 550b (which detecting region will form a pixel in the detected image), to be scanned across multiple regions of an array package 30 mounted on holder 599. The scanned regions for an array 112 will include at least the multiple features 116 of the array. In particular the scanning system is typically a line by line scanner, scanning the interrogating light in a line across an array 112 when at the reading position, in a direction of arrow 566, then moving ("transitioning") the interrogating light in a direction into/out of the paper as viewed in FIG. 5 to a position at an end of a next line, and repeating the line scanning and transitioning until the entire array 112 has been scanned. This can be accomplished by providing a housing 564 containing mirror 558 and focuser 560, which housing 564 can be moved along a line of pixels (that is, from left to right or the reverse as viewed in FIG. 5) by a transporter 562. The second direction 592 of scanning (line transitioning) can be provided by second transporter which may include a motor and belt (not shown) to move holder 599 along one or more tracks. The second transporter may use a same or different actuator components to accomplish coarse (a larger number of lines) movement and finer movement (a smaller number of lines). The reader of FIG. 5 may further include a reader (not shown) which reads an identifier from an array package 30. When identifier 40 is in the form of a bar code, that reader may be a suitable bar code reader.

An autofocus detector 570 is also provided to sense any offset between different regions of array 112 when in the reading position, and a determined position of the focal plane of the detection system. An autofocus system includes detector 570, processor 580, and a motorized adjuster to move holder in the direction of arrow 596. A suitable chemical array autofocus system is described in pending U.S. patent application Ser. No. 09/415,184 for "Apparatus And Method For Autofocus" by Dorsel et al., filed Oct. 7, 1999, incorporated herein by reference, as well as European publication EP 1091229 published Apr. 11, 2001 under the same title and inventors.

Controller 580 of the apparatus is connected to receive signals from detectors 550a, 550b (these different signals being different "channels"), namely a signal which results at each of the multiple detected wavelengths from emitted light for each scanned region of array 112 when at the reading position mounted in holder 599. Controller 580 also receives the signal from autofocus offset detector 570, and provides the control signal to EOM 510, and controls the scan system. Controller 580 may also analyze, store, and/or output data relating to emitted signals received from detectors 550a, 550b in a known manner. Controller 580 may include a computer in the form of a programmable digital processor, and include a media reader 582 which can read a portable removable media (such as a magnetic or optical disk), and a communication module 584 which can communicate over a communication channel (such as a network, for example the internet or a telephone network) with a remote site (such as a database at which information relating to array package 30 may be stored in association with the identification 40). Controller 580 is suitably programmed to execute all of the steps required by it during operation of the apparatus, as discussed further below. Alternatively, controller 580 may be any hardware or hardware/software combination which can execute those steps.

A feature of controller 580 is that it is programmed to at least reduce the effect on scale factor resulting from control point adjustment made in response to laser degradation over time. In many embodiments, a feature of the controller 580 is that it is programmed to maintain a constant scale factor as the laser degrades over time and during use of the scanner, where the constant scale factor is maintained by modulation of both: (a) the interrogating power, e.g., through adjustment of the power attenuator (e.g., EOM 510); and (b) detector gain, e.g., through modulation of the detector itself (such as changing the voltage of a PMT) or through use of additional detector attenuation devices (such as filters, etc.). By "constant scale factor" is meant that the scale factor changes insubstantially between first and second temporal points, e.g., from a time before a change in control point to a time after a change in control point, where the magnitude of any change between the two relevant time points does not exceed about 50%, usually does not exceed about 10% and more usually does not exceed about 5% or 1%, if it is detectable at all. This feature of the controller 580 and of the invention is seen schematically in FIG. 5, where two-way arrows join the controller 580 to the detectors 550a and 550b. In certain embodiments, the controller is programmed to adjust the laser attenuator to maintain a constant interrogating power even as the output power of the laser decreases due to laser degradation. Upon reaching the control point or a margin limit relative to the control point where selection of a new control point is required in order to maintain control loop stability, the controller then decreases the power output of the laser, establishes a new control point and modulates, e.g., increases, the detector gain in a manner sufficient to maintain a constant scale factor, despite the decrease in power output and selection of new control point.

Basically, the detector gain increases to compensate for the decrease in laser power while maintaining a constant scale factor. Where desired, the controller 180 can make the above adjustment in interrogating power and detector gain separately and independently for all channels of the scanner. Where a single light source excites more than one chromophore in more than one channel, the controller may then adjust all detectors appropriately, e.g., equally, in order to maintain a constant scale factor in each channel. As such, the controller is programmed in scanner devices according to the present invention in a manner that maintains a constant scale factor despite a transition of laser output and control point from a first value to a second value, e.g., in response to laser degradation.

Figure 6:
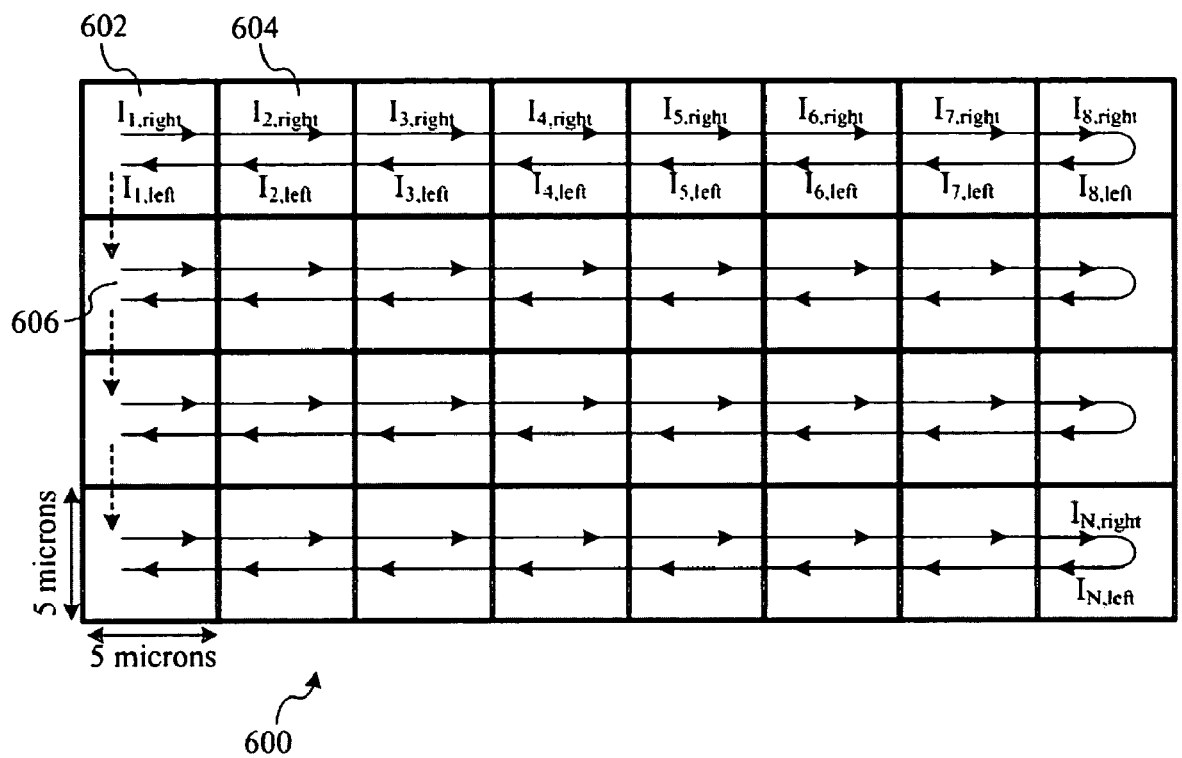
FIG. 6 depicts an exemplary embodiment of a scanning technique that reduces direction-dependent noise.

FIG. 6 depicts an exemplary embodiment of a scanning technique for correcting directional errors yielded from a fluorescence reader, such as the fluorescence reader of FIG. 5. FIG. 6 depicts a surface of a substrate 600, which is to be scanned by a fluorescence reader. As described previously in connection with FIG. 5, the reader operates by directing a laser 500a or 500b of a given wavelength at a region of the substrate, and by detecting fluorescence excited by the incident laser beam. (As mentioned previously, the reader may direct more than one wavelength of coherent light at the target, but for the sake of illustration, the following passages discuss scanning techniques with reference to a single wavelength of light emanating from a single laser.) Thus, the reader initiates operation by directing its laser 500a or 500b at a first region 602. The analytes upon the region 602 respond by fluorescing at a given intensity, determined in part by the concentration of the various analytes on the region 602 and the intensity of the laser beam focused thereupon. The intensity of the fluorescence is detected by the detector 550a or 550b, and is recorded in a memory device by the controller 580. This process of irradiating a region of the substrate and recording the fluorescence resulting therefrom is referred to herein as "scanning" a region.

After scanning the first region 602, the reader uses the transporter 562 to focus its laser upon an adjacent region 604, and to thereby scan that region 604. Again, the analytes upon the second region 604 respond by fluorescing at a given intensity, and the intensity of the fluorescence is detected by the detector 550a or 550b, and is recorded in a memory device by the controller 580. The reader continues scanning, on a region-by-region basis, moving left-to-right, until each of the regions in the first row has been scanned. (For the sake of illustration, each row is shown as including eight regions. In principle, a row may contain any number of regions, and usually contains thousands of such regions. Each region may, in principle, be of any size, but a typical region may be about 5 microns by 5 microns, as shown in FIG. 6.)

By virtue of the aforementioned process, each region of the first row has an intensity value corresponding thereto stored in the memory device. A given intensity value corresponds not only to a particular region, but also to a given scanning direction. Thus, the intensity value recorded for the first region 602 during the left-to-right scan of the first row may be termed $I_{1,right}$, and the intensity value recorded for the second region 604 during the left-to-right scan of the first row may be termed $I_{2,right}$ and so on.

After reaching the end of the first row, the transporter 162 reverses directions, and the first row is re-scanned, this time in a right-to-left direction, as shown in FIG. 6. Accordingly, each region in the first row is scanned twice—once in a left-to-right direction (the intensity recorded therefrom is termed $I_{M,right}$) and once in a right-to-left direction (the intensity recorded therefrom is termed $I_{M,left}$). Upon reaching the end of the first row (i.e., upon reaching region 602), the holder 599 is moved (e.g., by a belt and motor), so that the laser beam is incident upon the first region of the second row 606, whereupon the left-to-right scanning process, followed by the right-to-left scanning process, is again carried out. Therefore, for a given region of the substrate, region$_M$, two intensity values are recorded, $I_{M,right}$ and $I_{M,left}$.

As mentioned previously, the intensity value recorded for a given region of the substrate is distorted by various error sources, some of which are sensitive to the direction of the scanning process. Accordingly, for a given region of the substrate, region$_M$, the two intensity values recorded therefor, $I_{M,right}$ and $I_{M,left}$, are likely to differ in quantity, due at least to Gaussian noise and to directional error. To reduce the presence of both the Gaussian noise and the directional error, the two intensity values recorded for each region may be averaged, and the averaged values may be agglomerated into a bit-mapped graphic file, such as a TIFF file, for example. Thus, each pixel in the graphic file corresponds to the averaged values of $I_{M,right}$ and $I_{M,left}$:

$$Pixel_M = \sum_{M=1}^{N} 1/2 [I_{M,Right} + I_{M,Left}],$$

where N represents the total number of regions on the substrate, which also relates to the number of pixels in the graphic file.

The aforementioned process exhibits certain drawbacks in certain situations. For example, in some instances, users of the fluorescence readers wish to realize a relatively great dynamic range from the reader. (The detectors 150a and 150b of the reader saturate if an incoming signal is too strong, and do not provide a reliable reading if the signal is too weak. Hence, the dynamic range of the reader is the ratio of maximum non-saturating signal to minimum signal detectable with a given level of confidence.) To achieve this, the substrate may be scanned twice: a first time with a photomultiplier in the detector 150a or 150b set to achieve a relatively low gain, so that the particularly fluorescent regions of the substrate are not as apt to saturate the detectors 150a or 150b, and a second time with the aforementioned photomultiplier set to achieve a relatively high gain, so that the weakly fluorescent region of the substrate emit a signal of sufficient strength that it can be can be detected with the aforementioned given level of confidence. Accordingly, two images are created—one for each time the substrate is scanned. Thereafter, features may be extracted from each image, and the extracted data are then combined into a single data file, as described in U.S. patent application Ser. No. 10/262,124, entitled "BIPOLYMER ARRAY SCANNER WITH REAL-TIME SATURATION DETECTION," filed Sep. 30, 2002, which is hereby incorporated by reference for all it teaches. Alternatively, the two images may be directly combined into a single image that presents data of a relatively wide range of intensity values.

Because the two substrates are scanned twice, if the technique of FIG. 6 is employed for each scan, each row would be scanned four times over, meaning that the process becomes lengthy. To reduce the lengthiness of the process, while still achieving the reduction in direction-sensitive noise, the scanning technique depicted in FIGS. 7 and 8 may be employed. It is to be noted that the following scanning techniques may be used to address any eventuality in which the scan process of FIG. 6 proves to be undesirably lengthy.

Figure 7:
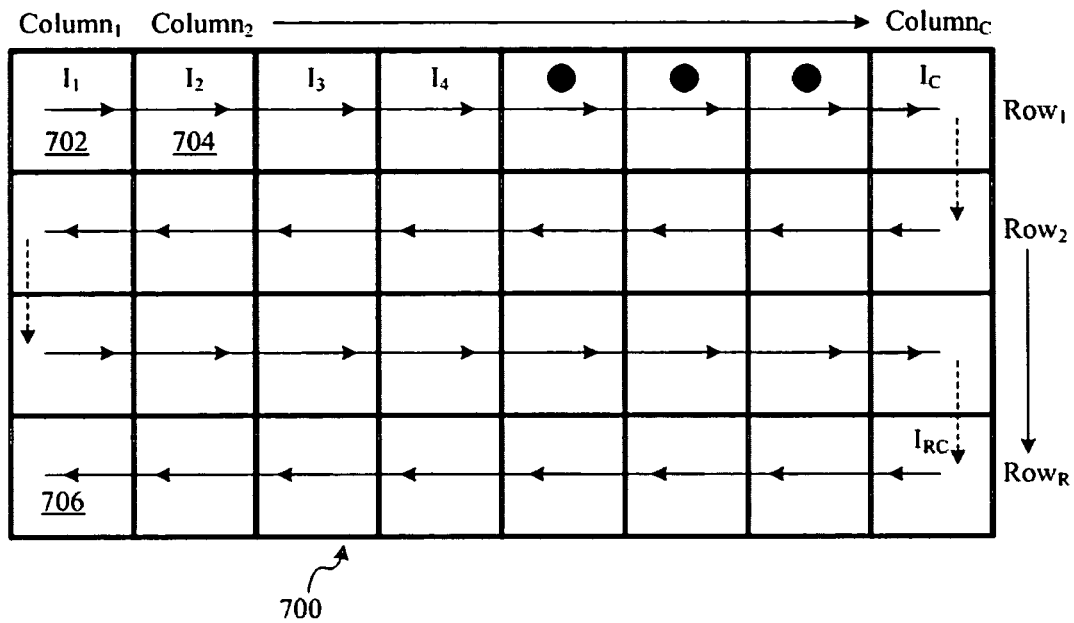
FIG. 7 depicts another exemplary embodiment of a scanning technique that reduces direction-dependent noise, and which may be carried out more quickly than the technique of FIG. 6.

FIG. 7 depicts a surface of a substrate 700, which is to be scanned by a fluorescence reader (again, the regions may be 5 microns by 5 microns, or may be of any other size, in principle). The reader initiates its operation by directing its laser 500a or 500b at a first region 702. After scanning the first region 702 and recording the fluorescence intensity value detected therefrom, the reader uses the transporter 562 to focus its laser upon an adjacent region 704, and to thereby scan that region 704. Again, the analytes upon the second region 704 respond by fluorescing at a given intensity, and the intensity of the fluorescence is detected by the detector 550a or 550b, and is recorded in a memory device by the controller 580. The reader continues scanning, on a region-by-region basis, moving left-to-right, until each of the regions in the first row has been scanned. (Although the scanning operation has been described herein as occurring via a mobile optics arrangement and a static target, the scanning operation may be accomplished with a static optics arrangement and a mobile target.)

Unlike the method of FIG. 6, the first row is not rescanned upon arrival at the final region therein. Instead, once the first row has been completely scanned, the holder 599 is moved, so that the laser beam is incident upon the final region of the second row 706, whereupon a right-to-left scanning process is carried out. Therefore, the surface of the substrate 700 is scanned on a line-by-line basis, with successive line being scanned in opposite directions. Accordingly, for a given region of the substrate, region$_M$, only one intensity value, I$_M$, is recorded.

The intensity values yielded from the process of FIG. 7 exhibit directional errors, meaning that intensity values observed in even numbered rows tend to be somewhat uniformly elevated or depressed by some constant value. Similarly, the intensity values observed in odd numbered rows tend to be somewhat uniformly elevated (if the even numbered rows were depressed) or depressed (if the even numbered rows were elevated) by some constant value. This effect expresses itself in a sort of "sawtooth" pattern of error.

Figure 8:
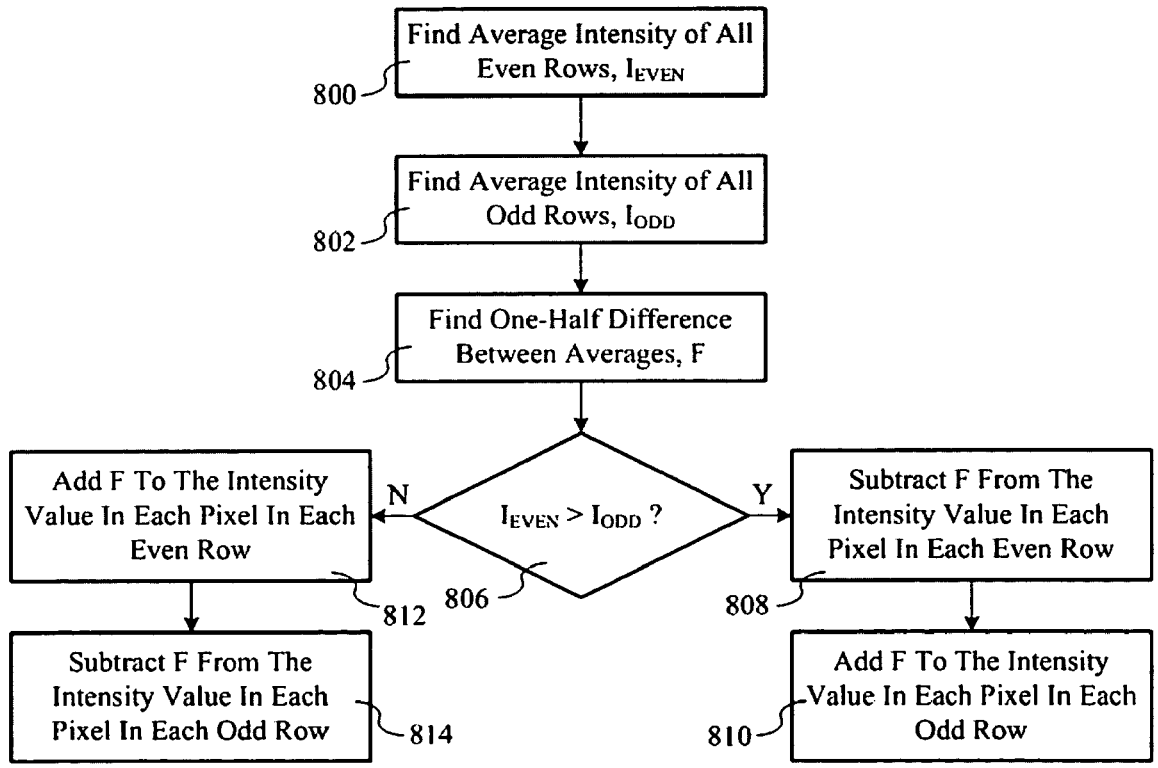
FIG. 8 depicts an exemplary embodiment of a method of processing the data developed by the scanning technique of FIG. 7.

To remove the directional errors observed in the intensity values yielded by the scanning technique of FIG. 7, a post-scanning manipulation of the intensity values may be employed. FIG. 8 depicts an exemplary embodiment of such a post-scanning manipulation. As can be seen from FIG. 8, the manipulation of the intensity values commences with finding the average of the intensity values detected in the regions of the even-numbered rows (operation 800). Additionally, the average of the intensity values detected in the regions of the odd-numbered rows are found (operation 802). Next, as shown in operation 804, the difference between the averages found in operations 800 and 802 is calculated, and the difference between the averages is divided by two. Thereafter it is determined whether the average intensity values measured in the regions of the even rows is greater than the average intensity values measured in the regions of the odd rows (operation 806). If so, then the value that was found in operation 804 is subtracted from each of the intensity values measured in even rows, and the aforementioned value is added to the intensity values measured in the odd rows (operations 808 and 810). If not, then the value that was found in operation 804 is added to each of the intensity values measured in even rows, and the aforementioned value is subtracted from the intensity values measured in the odd rows (operations 808 and 810). Alternatively, the difference between the averages found in operations 800 and 802 may be added to either the even or odd rows, depending upon which is dimmer (i.e., if the odd rows are dimmer, then the aforementioned difference is added to the odd rows, and if the even rows are dimmer, then the aforementioned difference is added to the even rows).

After execution of the method of FIG. 8, the resulting data may be stored in a graphic file format, such as a TIFF file or other file format. Of course, the method of FIG. 8 may be performed upon a data set that has already been converted to a TIFF file and possibly undergone further processing, as opposed to being executed upon the raw data. According to some embodiments of the invention, the quantity arrived at in operation 804 may be stored in the header of the graphics file (e.g., TIFF file), along with an indication of whether the aforementioned quantity was added/subtracted to/from odd/even rows, thereby allowing reconstruction of the original data, if desired.

The effect of the foregoing steps is to identify a baseline upon which intensity values measured in even-numbered rows ride, and a baseline upon which intensity values measured in odd-numbered rows ride. Then, the intensity values in even-numbered and odd-numbered rows are manipulated, so that they ride upon the same baseline.

It should be noted that the aforementioned processing scheme may be executed by any computing system, including a general computing system, and including by the controller 580 (FIG. 5). It should be further be noted that the aforementioned processing scheme may be performed upon either the raw fluorescent intensity values, as described with reference to FIGS. 7 and 8, or upon values derived therefrom, such as upon values having been generated in the wake of feature extraction, etc.

In some instances, it may be the case that the directional noise exhibited by any given measurement performed by a scanning device is substantially the same from measurement to measurement and from substrate to substrate. In such a situation, the quantity arrived at in operation 804 is substantially a constant (e.g., is substantially the same each time the value is calculated). In such circumstances, the constant value may be stored in the memory device associated with the controller 580, may be stored in a memory device of the computer executing the method of FIG. 8, or may be stored in any memory device and communicated to the computer performing the method of FIG. 8. Further, the method of FIG. 8 may be altered, so as to omit steps 800-804, and to access the stored constant in lieu of calculation of the constant.

Figure 9:
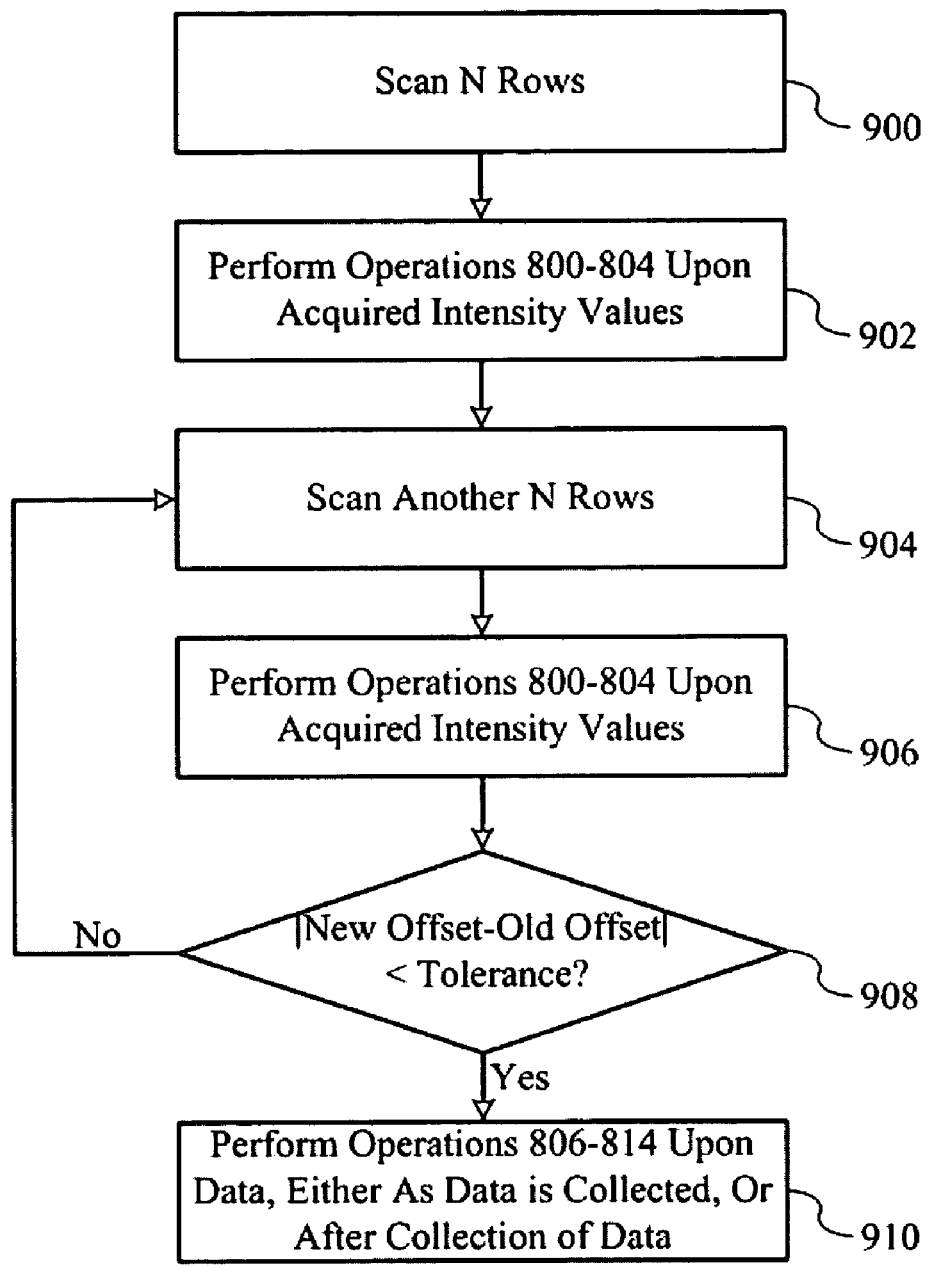
FIG. 9 depicts an embodiment of a variation of the method depicted in FIG. 8.

FIG. 9 depicts a variation of the method depicted in FIG. 9. As shown in FIG. 9, the variation begins with the scanning of a quantity of N rows, wherein N is an integer greater than or equal to one (operation 900). Thereafter, as shown in operation 902, operations 800-804 of the method of FIG. 8 are performed upon the data acquired in operation 900, thereby calculating an offset value. Thereafter, another N rows are scanned (operation 904), and another offset value is arrived at (operation 906). Then, in operation 908, it is determined whether the newly calculated offset value differs significantly from the previously calculated offset value. For example, it may be determined whether the absolute value of the difference between the newly calculated offset value and the previously calculated offset values is less than or equal to a threshold. If the newly calculated offset value differs significantly from the previously calculated value, control returns to operation 904, and another N rows are scanned. On the other hand, if the newly calculated offset value does not differ significantly from the previously calculated value, then operations 806-814 are performed upon the data obtained from the scanning operation, either as the data is acquired, or after acquisition of the data (operation 910).

The effect of the method of FIG. 9 is to arrive at the offset value of operation 804 (FIG. 8), without having to completely scan the entirety of a surface of a substrate. Instead, the offset value is periodically calculated as the scanning operation proceeds. Once the offset value converges to within an acceptable tolerance of a final value (e.g., a limit), the last-calculated threshold value is used for correction of the scanned data set. Such a procedure may, in some circumstances, speed up the process of reducing directional errors in scanned data.

In some instances, a scanner may impose a directional gain factor (i.e., a gain factor of $G_1$ is imposed upon intensity values of regions having been scanned in one direction, while a gain factor of $G_2$ is imposed upon intensity values of regions having been scanned in the other direction). In such circumstances (and other circumstances as well), the method of FIG. 10 may be useful.

Figure 10:
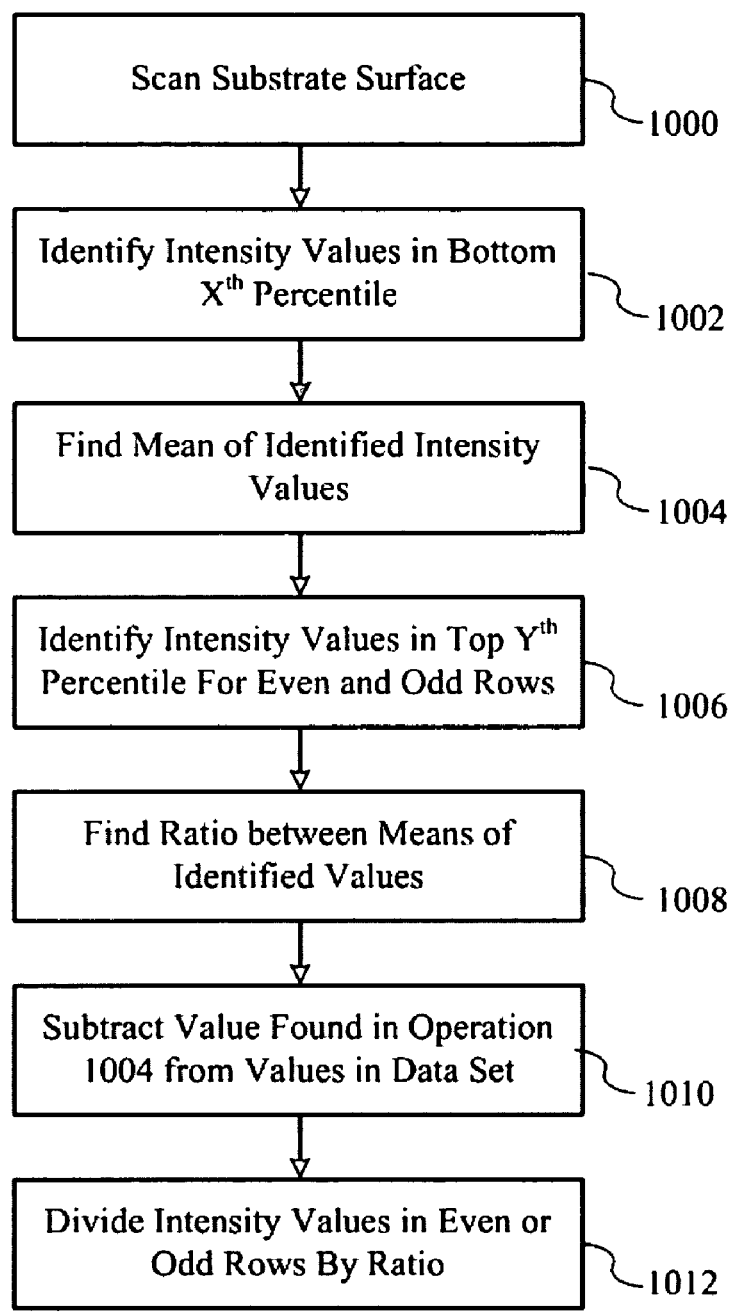
FIG. 10 depicts another exemplary embodiment of a method of processing the data developed by the scanning technique of FIG. 7.

As shown in FIG. 10, the method therein commences with scanning the surface of the substrate to be analyzed (operation 1000). Thereafter, as shown in operation 1002, the intensity values in the bottom Xth percentile are obtained. X is chosen so as to identify the "background" noise in the scanned intensity value (e.g., bottom 1%, 2%, 3%, 4%, 5%, etc. of intensity values). The intensity values identified in operation 1002 are then averaged, as shown in operation 1004, thereby arriving at a background noise value.

As shown in operation 1006, the top Yth percentile of intensity values for the even and odd rows are found. Y is chosen, so as to identify intensity values in which gain effects are evident (e.g., 90th percentile, 95th percentile, 96th percentile, 97th percentile, 98th percentile, 99th percentile, etc.). The intensity values identified in operation 1006 for even and odd rows are then averaged, arriving at an average for even rows and an average for odd rows; the ratio between these averages is found (operation 1008).

Thereafter, as shown in operation 1010, the background noise found in operation 1004 is subtracted from each of the intensity values in the data set. Finally, either the intensity values in regions of even or odd rows (which ever exhibits a greater mean intensity) are scaled down by the ratio found in operation 1008, so as to remove the directional gain.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

The invention claimed is:

1. A computerized method of scanning a plurality of fluorescent regions of a substrate, the regions being organized in rows, the method comprising:
    scanning a first plurality of rows in a first direction, thereby obtaining a first plurality of fluorescent intensity values, each value in the first plurality of fluorescent intensity values corresponding to regions in the first plurality of rows;
    scanning a second plurality of rows in a second direction that is opposite the first direction, thereby obtaining a second plurality of fluorescent intensity values, each value in the second plurality of fluorescent intensity values corresponding to regions in the second plurality of rows; and
    adjusting quantities standing in known relation to the first and second plurality of fluorescent intensity values to reduce directional errors observed in the first and second plurality of fluorescent intensity values.

2. The computerized method of claim 1, wherein the act of adjusting quantities standing in known relation to the first and second plurality of fluorescent intensity values comprises:
    finding an average of the first plurality of fluorescent intensity values;
    finding an average of the second plurality of fluorescent intensity values; and
    adjusting the first and second plurality of fluorescent intensity values based upon the averages of the first and second plurality of fluorescent intensity values.

3. The computerized method of claim 2, wherein the act of adjusting quantities standing in known relation to the first and second plurality of fluorescent intensity values based upon the averages of the first and second plurality of fluorescent intensity values comprises:
    finding a difference between the first and second plurality of fluorescent intensity values; and
    adjusting the first and second plurality of fluorescent intensity values based upon the difference between the averages of the first and second plurality of fluorescent intensity values.

4. The computerized method of claim 3, wherein the act of adjusting quantities standing in known relation to the first and second plurality of fluorescent intensity values based upon the difference between the averages of the first and second plurality of fluorescent intensity values comprises:
    adding or subtracting one-half of the difference between the averages of the first and second plurality of fluorescent intensity values to or from the first and second pluralities of intensity values.

5. The computerized method of claim 4, wherein one-half of the difference between the averages of the first and second plurality of fluorescent intensity values is added to the first plurality of fluorescent intensity values if the average of the first plurality of fluorescent intensity values is less than the average of the second plurality of fluorescent intensity values, and wherein one-half of the difference between the averages of the first and second plurality of fluorescent intensity values is subtracted from the first plurality of fluorescent intensity values if the average of the first plurality of fluorescent intensity values is greater than the average of the second plurality of fluorescent intensity values.

6. The computerized method of claim 1, wherein the act of adjusting quantities standing in known relation to the first and second plurality of fluorescent intensity values comprises adjusting values derived from the first and second plurality of fluorescent intensity values.

7. The computerized method of claim 1, wherein the regions are scanned on a row-by-row basis, with successive rows being scanned in opposite directions.

8. The computerized method of claim 1, wherein the act of adjusting quantities standing in known relation to the first and second plurality of fluorescent intensity values is performed during scanning of the plurality of fluorescent regions of the substrate.

9. The computerized method of claim 1, wherein the act of adjusting quantities standing in known relation to the first and second plurality of fluorescent intensity values is performed after scanning of the plurality of fluorescent regions of the substrate.

10. The computerized method of claim 1, wherein the act of adjusting quantities standing in known relation to the first and second plurality of fluorescent intensity values is performed prior to generation of a graphic file presenting the first and second pluralities of fluorescent intensity values.

11. The computerized method of claim 1, wherein the quantities standing in known relation to the first and second plurality of fluorescent intensity values comprise values in a graphics file.

12. The computerized method of claim 11, wherein the graphics file comprises a TIFF file.

13. The computerized method of claim 1, wherein the act of adjusting quantities standing in known relation to the first and second plurality of fluorescent intensity values comprises:
    finding a first mean of values that are within the first plurality of intensity values and that fall above a particular percentile, the particular percentile chosen so as to identify directional gain effects;
    finding a second mean of values that are within the second plurality of intensity values and that fall above the particular percentile, the particular percentile chosen so as to identify directional gain effects; and
    adjusting the quantities standing in known relation to the first and second plurality of fluorescent intensity values, based upon the first and second means, so as to reduce directional errors observed in the first and second plurality of fluorescent intensity values.

14. The computerized method of claim 1, wherein the act of adjusting quantities standing in known relation to the first and second plurality of fluorescent intensity values comprises:
    finding a mean of values that are within the first and second plurality of intensity values and that fall beneath a particular percentile, the particular percentile chosen so as to identify noise in the intensity values; and
    adjusting the quantities standing in known relation to the first and second plurality of fluorescent intensity values, based upon the mean.

15. A computer comprising:
    a processor; and
    a memory in communication with the processor, the memory storing a set of instructions that when executed cause the processor to perform acts comprising:
        scanning a first plurality of rows in a first direction, thereby obtaining a first plurality of fluorescent intensity values, each value in the first plurality of fluorescent intensity values corresponding to regions in the first plurality of rows;
        scanning a second plurality of rows in a second direction that is different from the first direction, thereby obtaining a second plurality of fluorescent intensity values, each value in the second plurality of fluorescent intensity values corresponding to regions in the second plurality of rows; and
        adjust quantities standing in known relation to the first and second plurality of fluorescent intensity values to reduce directional errors observed in the first and second plurality of fluorescent intensity values.

16. The computer of claim 15, wherein the memory further stores instructions that, when executed, cause the processor to perform the following acts:
    find an average of the first plurality of fluorescent intensity values;
    find an average of the second plurality of fluorescent intensity values; and
    adjust the first and second plurality of fluorescent intensity values based upon the averages of the first and second plurality of fluorescent intensity values.

17. The computer of claim 15, wherein the memory further stores instructions that, when executed, cause the processor to adjust quantities standing in known relation to the first and second plurality of fluorescent intensity values, during scanning of the plurality of fluorescent regions of the substrate.

18. The computer of claim 15, wherein the memory further stores instructions that, when executed, cause the processor to adjust quantities standing in known relation to the first and second plurality of fluorescent intensity values, after scanning of the plurality of fluorescent regions of the substrate.

19. The computer of claim 15, wherein the quantities standing in known relation to the first and second plurality of fluorescent intensity values comprise values in a graphics file.

20. The computer of claim 15, wherein the memory further stores instructions that, when executed, cause the processor to perform the following acts:
    find a first mean of values that are within the first plurality of intensity values and that fall above a particular percentile, the particular percentile chosen so as to identify directional gain effects;
    find a second mean of values that are within the second plurality of intensity values and that fall above the particular percentile, the particular percentile chosen so as to identify directional gain effects; and
    adjust the quantities standing in known relation to the first and second plurality of fluorescent intensity values, based upon the first and second means, so as to reduce directional errors observed in the first and second plurality of fluorescent intensity values.

* * * * *